United States Patent [19]
Macris et al.

[11] Patent Number: 4,989,596
[45] Date of Patent: Feb. 5, 1991

[54] FACE CHAMBER

[76] Inventors: Allen G. Macris, 416 Johnson Ferry Rod., N.W., Atlanta, Ga. 30328; Stothe P. Kezios, 1060 Winding Creek Trail, N.W., Atlanta, Ga. 30328; Harry L. Vaughan, 3482 Sweetwater Dr., Lawrenceville, Ga. 30245

[21] Appl. No.: 311,128
[22] Filed: Feb. 14, 1989
[51] Int. Cl.$^5$ ............................................. A62B 18/10
[52] U.S. Cl. ........................... 128/201.28; 128/206.24; 128/207.12; 128/206.28
[58] Field of Search ............. 128/201.12, 201.22, 128/201.23, 201.24, 201.25, 201.28, 204.18, 204.26, 205.17, 205.25, 206.15, 206.22, 206.24, 206.26, 206.27, 206.28, 207.11, 207.12

[56] References Cited
U.S. PATENT DOCUMENTS

| | | | |
|---|---|---|---|
| 1,050,621 | 1/1913 | Ford | 128/206.28 |
| 1,695,170 | 12/1928 | Burdiex | 128/207.12 |
| 1,960,544 | 5/1934 | Malcom | 128/206.26 |
| 2,222,971 | 11/1940 | Wright | 128/207.12 |
| 2,238,492 | 4/1941 | Leguillon | 128/206.28 |
| 3,018,776 | 1/1962 | Saitta et al. | 128/206.26 |
| 3,044,464 | 7/1962 | Gray | 128/206.26 |
| 3,097,642 | 7/1963 | Russell | 128/206.24 |
| 3,330,273 | 7/1967 | Bennett | 128/206.26 |
| 3,330,274 | 7/1967 | Bennett | 128/207.11 |
| 3,343,535 | 9/1967 | Lytle et al. | 128/206.24 |
| 3,441,020 | 4/1969 | Wortz et al. | 128/207.11 |
| 4,354,520 | 10/1982 | Easly, Jr. | 128/207.12 |
| 4,402,316 | 9/1983 | Gadberry | 128/206.24 |

FOREIGN PATENT DOCUMENTS

| | | | |
|---|---|---|---|
| 233473 | 7/1944 | Switzerland | 128/206.26 |
| 483502 | 4/1938 | United Kingdom | 128/207.12 |

Primary Examiner—Eugene R. Eickholt
Attorney, Agent, or Firm—B. J. Powell

[57] ABSTRACT

A face chamber for use with a continuous positive airways pressure apparatus to treat a patient comprising a housing with a pressure chamber and a face receiving opening to fit over the patient's face, a seal to seal the patient's face to the housing so that the patient breathes into said pressure chamber, an inlet connector for connecting the output of the continuous positive airways pressure apparatus to the pressure chamber, and control valves for controlling the discharge of gases from the face chamber.

9 Claims, 3 Drawing Sheets

FACE CHAMBER

BACKGROUND OF THE INVENTION

This invention relates generally to face chambers and more particularly to face chambers for use in continuous positive airways pressure treatment.

Patients who suffer respiratory distress are sometimes subjected to a continuous positive airway pressure treatment (CPAP) to assist the spontaneous breathing patient in breathing. This technique maintains a positive pressure (usually 1-30 cm. $H_2O$) in the respiratory system at all times. The benefits of positive pressure breathing have been repeatedly documented over the past three (3) decades in the medical literature. This treatment has been administered through an endotracheal tube or by face mask. On one hand, the mask devices available for the administration of positive airway pressure to the individual have certain disadvantages that limit their effectiveness and/or they have poor patient acceptance. On the other hand, the use of an endotracheal tube can effectively provide any desired volume of breathing under any range of pressures, but has a number of serious shortcomings and it creates life-threatening complications in addition to requiring intensive care facilities and expensive respiratory equipment during use.

Examples of this technique are set forth in the following articles:

(1) Gregory, et. al., *Treatment of the Idiopathic Respiratory—Distress Syndrome with Continuous Positive Airway Pressure*, 284 The New England Journal of Medicine 1333 (1971);

(2) Ahlstrom, et. al., *Continuous Positive Airways Pressure Treatment by a Face Chamber in the Idiopathic Respiratory Distress Syndrome*, 51 Archives of Disease of Childhood, 13 (1976);

(3) Greenbaum, et. al., *Continuous Positive Airway Pressure Without Tracheal Intubation In Spontaneously Breathing Patients*, 69 Chest 615 (1976); and (4) Covelli, et. al., *Efficacy of Continuous Positive Airway Pressure Administered By Face Mask*, 81 Chest 147 (1982).

In addition to the face masks and chambers set forth in the above articles, the following patents describe various face masks and helmets for other uses which are provided with various ventilation valves and effluent receivers:

| U.S. Pat. No. | Inventor  | Issue Date | Cl/SubCl   |
|---------------|-----------|------------|------------|
| 3,473,165     | Gran      | 10/21/69   |            |
| 3,550,588     | Stahl     | 12/29/70   | 128/141    |
| 3,603,313     | Arblaster | 09/07/71   | 128/275    |
| 4,249,527     | Ko        | 02/10/81   | 128/204.18 |
| 4,505,310     | Schneider | 03/19/85   | 141/114    |
| 4,537,189     | Vicenzi   | 08/27/85   | 128/202.13 |
| 4,583,246     | Griswold  | 04/22/86   | 2/2.1A     |
| 4,712,594     | Schneider | 12/15/87   | 141/114    |

None of the masks or face coverings illustrated in these cited patents are adapted especially for use in CPAP therapy. The face masks or coverings previously used in CPAP therapy were usually uncomfortable, bulky and cumbersome to use and usually required that the patient remain in a restricted environment while such therapy was being performed. Also, in many clinical situations, there are individuals who require more help than that which can be administered with the presently available support equipment short of endotracheal intubation.

The disadvantages of the face masks and devices now readily available for the administration of positive airway pressure are as follows:

(1) The seal of the face mask is incapable of maintaining an air-tight face-to-face interface continuously to provide the airway with a predictable positive pressure;

(2) After placement of the face mask, there is no easy access to the face that will allow the individual to eat, to drink, to swallow medication, to wipe the mouth, to cough and expectorate, to blow or scratch the nose, etc., short of its complete removal. (The performance of such small required or desired functions at times seem insignificant until they are deprived or restricted);

(3) The application of a mask to the face for the purpose of administering continuous positive airway pressure has always been fraught with the danger of aspiration of gastric contents into the lungs, a complication with dire consequences should a person vomit;

(4) A most serious shortcoming is the lack of patient acceptance of the presently available masks due to apprehension since most people perceive them as a means of suffocation rather than aid. (The almost universal reaction of the person is to tear or pull the mask off the face almost immediately); and (5) With the face mask applied typically over the nose and the mouth, the individual' speech becomes indistinct and difficulty in communication with the patient ensues.

It must be noted here that the introduction of an endotracheal tube into the larynx and trachea immediately deprives the patient of the ability to communicate by speech, literally confines the patient to bed, and requires a special team of nurses and respiratory therapists to provide care for now the patient's:

(1) swallowing has become difficult with the endotracheal tube in place;

(2) the evacuation of his tracheal bronchial secretions must be removed by mechanical suctioning of the endotracheal tube; and (3) communication is limited to scribbling on a pad, and for those possessing limited writing skills, to banging on the side-rails, etc. The presence of the endotracheal tube also necessitates the use of a nasogastric tube early in the patient's care in order to keep the stomach deflated, to lessen pressure in the left diaphragm, and to prevent aspiration around the cuffed endotracheal tube. Clinically, however, this is not always effective to eliminate aspiration. Besides, it has been shown that the presence of a nasogastric tube causes gastroesophageal reflux with all of its complications to the lower esophagus. Because of the presence of the endotracheal tube in the throat and the tube in the stomach, the person's nutrition and fluid requirements have to be maintained and/or replaced intravenously, and in most instances, by a line placed in a large central vein.

All of the above necessary paraphernalia placed into the patient's orifices and lumina, needless to say, add to one's discomfort and cause anxiety as well as pain and complications. These problems are delineated as follows: (1) aspiration pneumonitis is caused by gastric esophageal reflux; and (2) the suctioning of the tracheal bronchial tube leads to complications of nosocomial infections and/or pneumonia due to *Staphylococcus aureus*, *Pseudomonas aeruginosa* or other opportunistic infections. These complications are extremely difficult and costly to treat, may spread to other patients, and, at times, have caused tracheal stricture—a most severe and dreaded life-threatening complication.

The inability of the individual to speak to relatives or those caring for him (i.e., doctors, nurses and other paramedical personnel), as well as the restraining necessary to prevent the patient from forcefully removing the various tubes, leads to often occurring intensive care (ICU) psychosis. More commonly, however, the problem is one of a necessitating heavy sedation that impedes spontaneous breathing and prolongs the use of the respirator. Furthermore, the central intravenous catheter can lead to bacteremia, to lung abscesses, to bacterial endocarditis, and/or to fungal-type blood stream infections in immunosuppressed individuals.

Among the problems not mentioned above is the frequently serious decision of placing an individual whose ability to recuperate is uncertain on the respirator by way of an endotracheal tube. Then, that individual's course becomes protracted and without any foreseeable termination of mechanical respiratory support.

SUMMARY OF THE INVENTION

These and other problems and disadvantages associated with the prior art are overcome by the invention disclosed herein by providing a face chamber which can be used in CPAP therapy to deliver pressurized air and/or oxygen to the patient, which is comfortable and simple in design and construction so as to be easily used, which simplifies the amount of external control required to operate same, and which comfortably seals the face chamber to the patient over a wide range of face shapes and sizes. The realization of the need and the subsequent development of the mask of the invention has come from clinical observations over a period of twenty-seven (27) years in the private practice of thoracic surgery. The range and type of illness treated spans a gamut of acute pulmonary trauma, respiratory distress syndrome in the newborn, and the long-standing chronic pulmonary disabilities.

The face chamber can be made out of transparent material so that the patient's view is virtually unrestricted while wearing the face chamber. The face chamber is sized to fit over the patient's face from the chin to the forehead thereby permitting the sealing pressure to be spread over a wider area thus making the face chamber more comfortable to wear. Further, the face chamber is provided with an inflatable sealing arrangement which allows the face chamber to conform to a wide variety of sizes and shapes of faces. Further, the necessary control valves to control the operation of the CPAP therapy air and oxygen pressure in the face chamber are mounted directly on the face chamber itself so as to minimize the response time thereof. Further, a reservoir is provided on the face chamber which serves both as a collapsible gas reservoir to maintain a sufficient volume of breathing air and oxygen for the patient to breathe even where the patient intake of air and/or oxygen is well above the instantaneously volumetric flow rate of the CPAP apparatus.

The apparatus of the invention includes generally a housing including a cylindrical sidewall closed at one end by a circular end wall with the opposite end of the sidewall cut to conform to the patient's face. An inflatable seal assembly is provided around that end of the sidewall cut to conform to the patient's face and straps are provided to maintain the face chamber in position. The seal includes an inflatable member which is covered with a resilient sealing flap that actually engages the patient's face to both cushion and to seal it. An inlet connection assembly is provided which diffuses the incoming gas stream from the continuous positive airways pressure apparatus so as to divert a portion of the gas stream over the patient's face to cool it. Control valves are mounted in the sidewall of the housing so that the pressure within the pressure chamber can be regulated and the air can be drawn into the pressure chamber in the event the CPAP apparatus fails.

The apparatus also includes a combination gas reservoir/vomitous bag assembly which is mounted on the lower portion of the housing and serves to maintain a sufficient reservoir of gas for the patient to inhale without drawing in ambient air while at the same time serving as removable vomitous bag. The opening between the reservoir/bag assembly and the housing is located and sized so as to provide easy access to the patient's mouth and nose when the assembly is removed without having to remove the housing itself.

These and other features and advantages of the invention disclosed herein will become more apparent upon consideration of the following detailed description and accompanying drawings wherein like characters of reference designate corresponding parts throughout the several views and in which:

Figure 1:
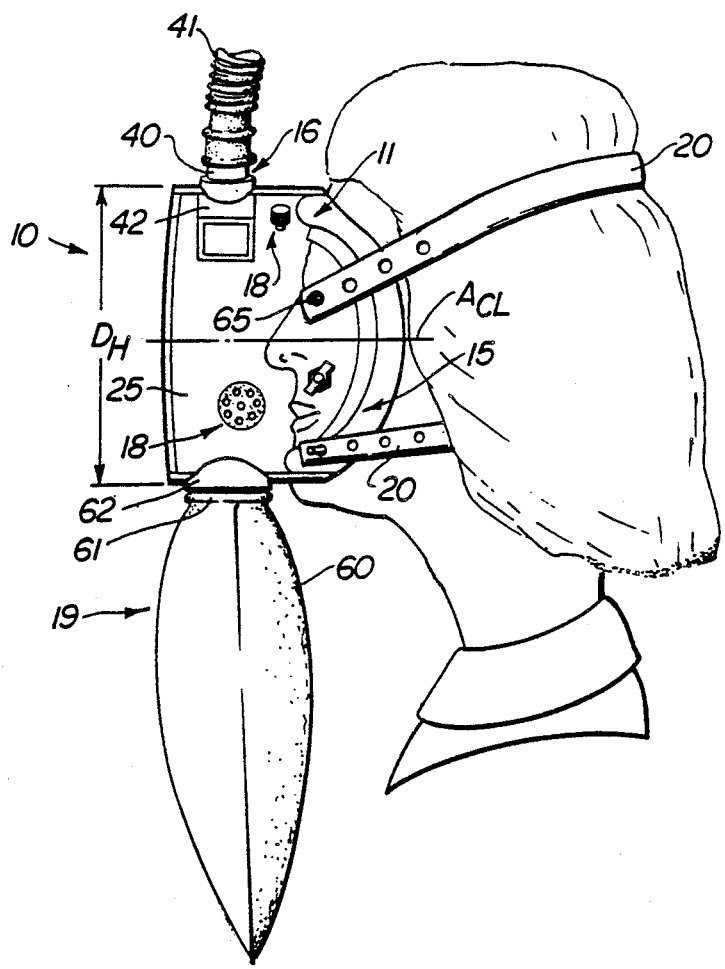
FIG. 1 is a side view illustrating the invention in use.

The figures and the following detailed description disclose specific embodiments of the invention; however, it is to be understood that the inventive concept is not limited thereto since it may be embodied in other forms or other uses.

DETAILED DESCRIPTION OF ILLUSTRATIVE EMBODIMENTS

It will be seen that the face chamber 10 embodying the invention is to be used with continuous airways positive pressure (CPAP) apparatus which produces a breathable gas stream typically including air and/or oxygen and/or other medicinal and/or other therapeutic vapors. This type of therapy is described in the literature. The face chamber 10 eliminates a number of the extra pieces of apparatus typically required for use with the prior art face masks or face chambers in that the control valve mechanisms are incorporated in the face chamber itself as will become more apparent. The face chamber 10 includes generally a housing 11 which defines a pressure chamber 12 therein and a face receiving opening 14 therethrough to the pressure chamber 12. A seal assembly 15 is mounted about the face receiving opening 14 to seal the housing 11 to the patient's face. An inlet connection assembly 16 is provided to connect the gas output of the CPAP apparatus or other vapor or gaseous sources to the face chamber 10 and also control the diffusion of the gas stream within the pressure chamber 12. Control valves 18 are mounted on the housing 11 and communicate with the pressure chamber 12 to regulate the pressure in the pressure chamber 12. A reservoir/vomitous bag assembly 19 is mounted on the housing 11 at the lower portion thereof. Straps 20 are provided that connect to the housing 11 and serve to maintain the face chamber 10 on the patient's face. The straps may be provided with a guide member at the back of the head.

The housing 11 includes a generally cylindrical sidewall 25 with a central axis $A_{CL}$ therethrough which serves as the central axis of the face chamber 10. While different configurations may be used, the distal end 26 of the sidewall 25 is normal to the central axis $A_{CL}$ while the face end 28 is cut to conform to the general facial shape of the patient as will become more apparent to define a sealing edge 29 therealong. Generally speaking, the sealing edge 29 has an upper forehead receiving section 30 and a lower chin receiving section 31 therein. The sidewall 25 is a substantially rigid member.

The distal end 26 of the sidewall 25 is closed by a generally circular end wall 32. The end wall 32 illustrated is also substantially rigid. While different configurations may be utilized, the end wall 32 is made out of a transparent material and so is the sidewall 25 so that the patient has substantially unrestricted viewing when wearing the face chamber. It will be appreciated that the diameter $D_H$ of the sidewall 25 is sufficient for the sealing edge 29 to extend about the patient's face beginning just below the patient's mouth and extending over the patient's eyes to the forehead. This serves to increase the size of the pressure chamber to assist in maintaining the necessary volume for operation while at the same time maximizing the comfort to the patient.

The seal assembly 15 is mounted on the sidewall of the housing 11 along the sealing edge 29. The sealing assembly 15 includes a tubular inflatable member 34 mounted on the inside of the sidewall 25 immediately adjacent the sealing edge 29 so that inflation of the member 34 causes the member to expand interiorly of the sidewall 25. The inflatable member 34 is made out of an elastomeric material so that inflation of the inflatable member 34 allows the member 34 to physically expand. A fill valve 35 is mounted on the housing 11 adjacent the inflatable member 34 and extends through the sidewall 25 interiorly of the inflatable member 34 so that air can be pumped into the inflatable member 34 through the fill valve 35 to selectively inflate the inflatable member 34. The fill valve 35 is provided with a one-way valve that allows air to enter the inflatable member but precludes it from leaving. The fill valve 35 is provided with a fill connector 36 which is adapted to fit on a conventional syringe so that the syringe can be used to pump up the inflatable member 34.

Mounted on the sidewall 25 along the sealing edge 29 is an elastomeric seal flap 38 which folds forwardly over the inflatable member 34 so that the flap 38 lies between the patient's face and the inflatable member 34. The seal flap 38 is made with a peripheral distance shorter than the periphery at which the face chamber 10 engages the patient's face so that the flap remains stretched and so that pressing the face chamber 10 against the patient's face causes the flap 38 to positively engage the patient's face. Further, as the inflatable member 34 is expanding, it further forces the seal flap 38 into contact with the patient's face. Thus, a wide range of patient's faces with different sizes and different facial configurations can be accommodated with chamber 10.

Figure 2:
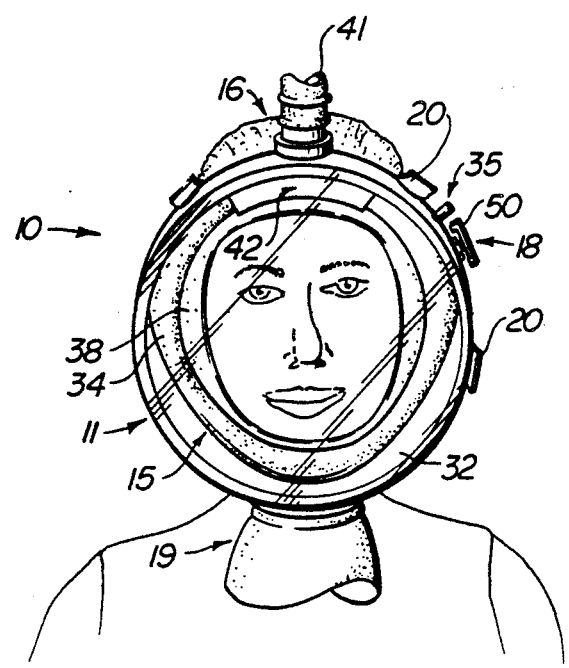
FIG. 2 is a face view illustrating the invention in use.
Figure 3:
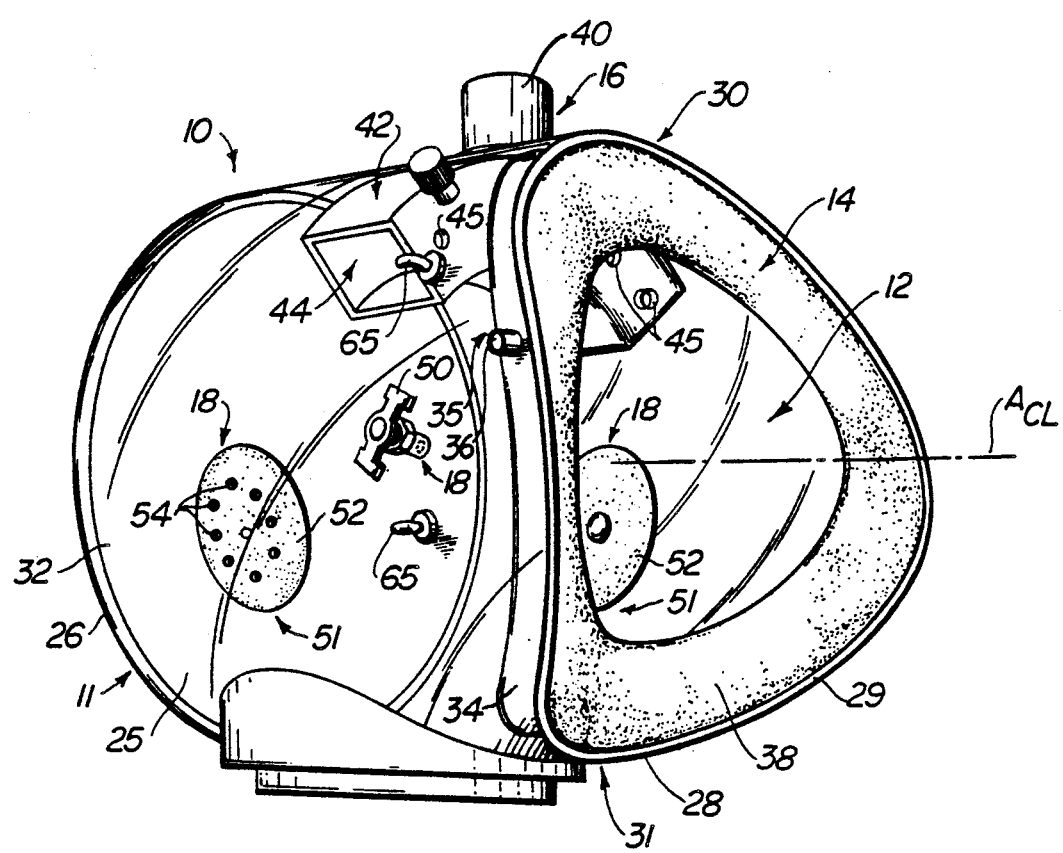
FIG. 3 is a prospective view illustrating the invention.

The inlet connection assembly 16 includes an inlet connector 40 adapted to be connected to the outlet hose 41 from the CPAP apparatus or other gas or vapor source and is mounted on the top of the housing 11 as seen in FIGS. 1 and 2. The inlet connector communicates with a tubular deflector member 42 mounted inside the sidewall 25 oriented in a plane generally normal to the axis $A_{CL}$ of the face chamber 10. The deflector member 42 is curved and terminates in the upper portion of the pressure chamber 12 but laterally of a vertical plane passing through the axis $A_{CL}$. The deflector member 42 defines a cross passage 44 therethrough which also extends along the transverse plane to the axis $A_{CL}$ so that the majority of the incoming gas stream is directed around the inside periphery of the sidewall 25 to ensure that all portions of the face chamber 12 are purged of any stale gasses. The deflector member 42 also defines a plurality of discharge holes 45 therethrough which face the patient's forehead so that a portion of the incoming gas stream is deflected over the patient's face and serves to cool the patient's face. The particular configuration of the deflector member 42 may be changed without departing from the invention.

The control valves 18 include a pressure regulating valve 50 mounted in the sidewall 25 so that the face chamber 12 can communicate with the atmosphere through valve 50. The pressure regulating valve 50 is designed to maintain the desired pressure level within the pressure chamber 12 so that the patient's breathing assist is provided. Pressure regulator valve 50 is adjustable so that the amount of pressure maintained in the pressure chamber can be regulated. This valve is also designed to limit the chamber 12 pressure to a preset value and will act in relief of chamber pressure in case of overpressure.

Also mounted on the sidewall 25 are a pair of intake valves 51. These valves serve to allow atmospheric air to enter the face chamber in the event the pressure in the face chamber drops below atmospheric pressure. The intake valve 51 include a resilient flap 52 mounted on the inside of the sidewall 25 with a plurality of intake holes 54 defined through the sidewall 25 in registration with the flap 52 so that the valve allows air to enter face chamber 12 from the atmosphere but precludes the passage of gas from the pressure chamber 12 to the atmosphere.

The reservoir/vomitous bag assembly 19 includes generally a bag 60 which is flexible and fluid tight and provided with an inlet connector 61. A housing connector 62 is provided through the lower portion of the sidewall 25 so that it will lie below the patient's mouth when in use and defines a opening therethrough. The housing connector 22 is selectively connectable to the inlet connector 61 on the bag 60 to seal the interior of bag 60 to the pressure chamber 12. The connection between the connectors 61 and 62 is such that the operating pressure for the CPAP can be imposed on the interior of the bag 60 without pushing the bag 60 off the inlet connector 61. The size of the bag 60 is selected such that a sufficient volume of gas is provided in combination with the pressure chamber 12 so that the volumetric flow rate into the patient's lungs can be accommodated without drawing in atmospheric air.

Second Embodiment

Figure 4:
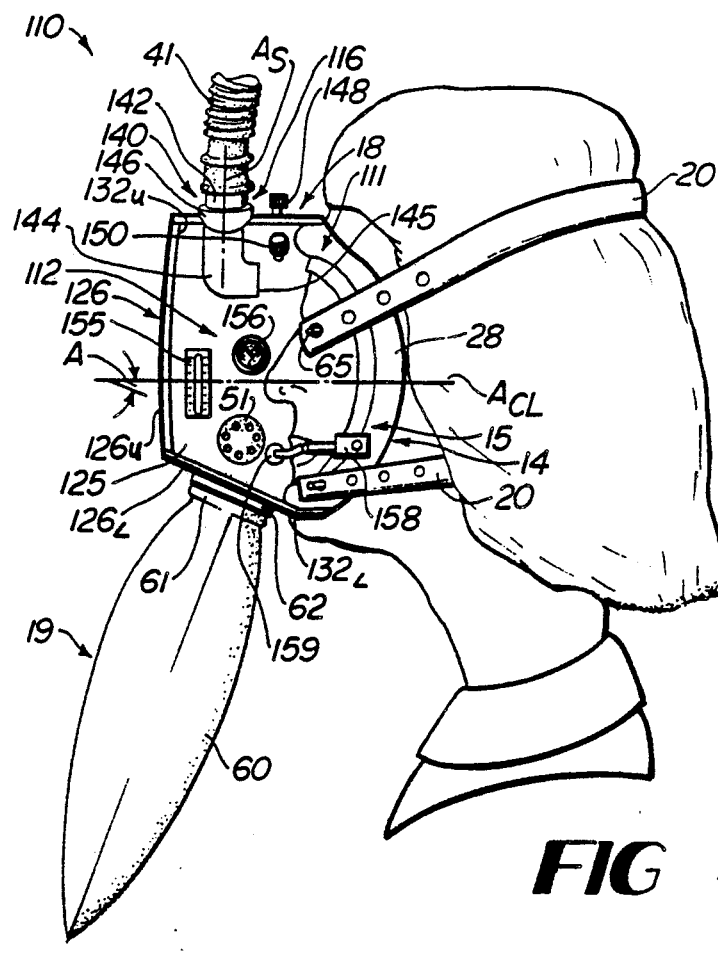
FIG. 4 is a side view similar to FIG. 1 of a second embodiment of the invention.
Figure 5:
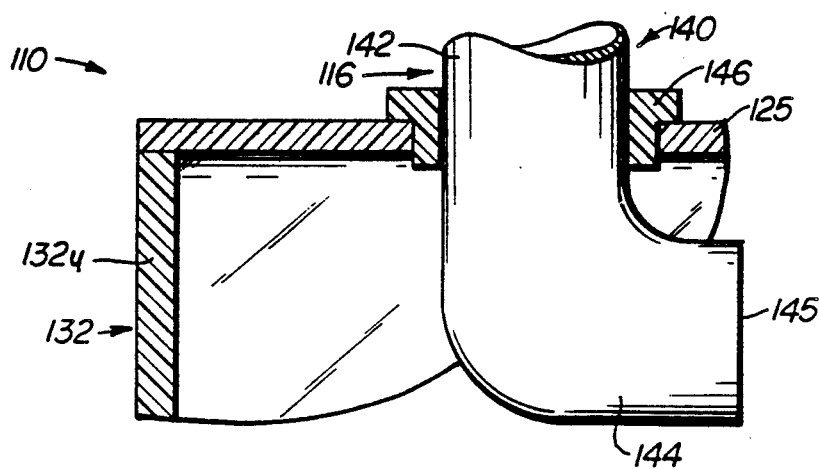
FIG. 5 is a partial longitudinal cross-sectional view of the embodiment of FIG. 4.

FIGS. 4 and 5 illustrate a second embodiment of the face chamber which has been designated 110. The face chamber 110 includes generally a housing 111 which defines a pressure chamber 112 therein and the face receiving opening 14 therethrough to the pressure chamber 112. Seal assembly 15 is also mounted about the face receiving opening 14 to seal the housing 111 to the patient's face. An inlet connection assembly 116 is provided to connect the gas output of the CPAP apparatus or other vapor or gaseous sources to the face chamber 110 and also control the diffusion of the gas stream within the pressure chamber 112. A control valve arrangement 118 is mounted on the housing 11 and communicates with the pressure chamber 12 to regulate the pressure in the pressure chamber 112. The reservoir/vomitous bag assembly 19 is also mounted on the housing 111 and straps 20 are provided that connect to the housing 111 and serve to maintain the face chamber 110 on the patient's face.

The housing 111 includes a generally cylindrical sidewall 125 with a central axis $A_{CL}$ therethrough which serves as the central axis of the face chamber 110. The distal end 126 of the sidewall 125 has an upper portion $126_U$ that is normal to the central axis $A_{CL}$ and a lower portion $126_L$ that is cut back to form an included angle $A_1$ with axis $A_{CL}$, usually 30°–35°. The face end 28 is cut like that of chamber 10. The sidewall 125 is also a substantially rigid member.

The distal end 26 of the sidewall 25 is closed by an end wall 32 with an upper semicircular portion $132_U$ closing portion $126_U$ and an angled lower portion $132_L$ closing portion $126_L$. The end wall 132 illustrated is also substantially rigid. While different configurations may be utilized, the end wall 132 also may be made out of a single piece of transparent material or with different materials for the different positions.

The inlet connection assembly 116 includes an inlet tube 140 adapted to be connected to the outlet hose 41 from the CPAP apparatus or other gas or vapor source and is slidably mounted through the top of the housing 111 as seen in FIG. 5. The inlet tube 140 has a straight inlet portion 142 slidably received through a sealing bushing 146 in the top of side wall 125 along a slide axis $A_S$ generally normal to the axis $A_{CL}$ of the face chamber 110. The tube 140 has a discharge portion 144 on its inboard and oriented normal to the tube axis and generally parallel to axis $A_{CL}$. Thus, the tube 140 can slide in and out along a radius of side wall 125 and also rotated in bushing 146 to locate the discharge opening 145 from tube 140 relative to the patient's face. Thus, the incoming gas stream is deflected over the patient's face and serves to cool the patient's face.

The control valve arrangement 118 includes a flow control valve 148 that serves to regulate the volumetric flow rate of gas through the face chamber 112 and a pressure regulating valve 150 designed to maintain the desired pressure level within the face chamber 12 so that the patient's breathing assist is provided. Both flow control valve 148 and the pressure regulator valve 150 may be adjustable so that the volumetric flow rate and the pressure maintained in the pressure chamber 112 can be regulated. Also mounted on the sidewall 125 are the intake valves 51.

The reservoir/vomitous bag assembly 19 is connected to the lower portion $132_L$ of the end wall 132 through the housing connector 62 so that it will lie below the patient's mouth when in use. The opening through the connector 62 provides access to the patient's face when the bag 60 is removed.

A thermometer 155 as seen in FIG. 4 may be provided to indicate the temperature inside the face chamber 112. The thermometer 155 may be analog or digital. A pressure gauge 156 may also be provided to indicate the pressure in chamber 112.

To provide a communication link, a transmitter 158 may be provided with a microphone 159 as seen in FIG. 4. This will allow an appropriate receiver (not shown) to be used to hear the patient either proximally or at a distance.

We claim:

1. A face chamber for use with a continuous positive airways pressure source to treat a patient with the pressurized output gasses therefrom comprising:

a generally cylindrical, substantially rigid annular sidewall having a central axis, said sidewall having opposed ends, an upper portion and a lower portion; one of said ends being open and defining a sealing edge thereon contoured to generally conform to the patient's face; said sidewall having a diameter such that the sidewall extends around the patient's face from the chin to the forehead;

an end wall joined to and closing that end of said sidewall opposite said sealing edge; said end wall having a first substantially transparent portion oriented generally normal to the sidewall central axis and closing the upper portion of the open end of said sidewall so that the patient may see therethrough when said face chamber is in place on the face of the patient;

a face seal along said sealing edge of said sidewall adapted to seal the sealing edge to the face of the patient;

means for holding said sidewall on the face of the patient and maintain said seal in sealing contact with the patient's face, said sidewall and said end wall defining a closed pressure chamber about the patient's face while said face chamber is seated against the patient's face so that the patient's face contacts said face chamber only along said seal to free the patient's face and permit the patient to talk and eat without having to remove said face chamber; and inlet connection means mounted on said face chamber for connecting the output gasses of the continuous positive airways pressure source to said pressure chamber.

2. The face chamber of claim 1
   wherein said end wall further includes a lower portion closing the lower portion of the end of said sidewall opposite the sealing edge and defining an acute angle with the central axis of said sidewall, said lower portion of said end wall defining an access opening therethrough sized to permit manual access to the patient's mouth and nose when said face chamber is installed on the patient's face; and, closure means for selectively closing said access opening to permit the continuous positive airways pressure source to pressurize the pressure chamber.

3. The face chamber of claim 2 wherein said closure means further includes a reservoir assembly comprising:

a reservoir connector mounted on said end wall around said access opening; and an inflatable reservoir bag removably mounted on said reservoir connector exteriorly of said housing so that said reservoir bag communicates with said pressure chamber through said access opening to act as a reservoir for the gases in said pressure chamber to permit the patient to inhale from said pressure chamber without drawing atmospheric air thereinto.

4. The face chamber of claim 3 wherein said inlet connection means is located in the upper portion of said sidewall and further includes a discharge portion defining an outlet therefrom oriented generally parallel to the central axis of said side wall, said discharge portion pivotal about an axis generally radially oriented with respect to said sidewall to change the position at which the incoming gasses from the continuous positive airways pressure source are directed onto the patient's face.

5. The face chamber of claim 4 wherein said discharge portion on said connection means is further movable along a positioning axis generally radially with respect to said sidewall so that the position at which the incoming gasses from the continuous positive airways pressure source are directed onto the patient's face can be moved.

6. The face chamber of claim 2 wherein said face seal includes:
   a resilient sealing flap connected to said sidewall about said sealing edge and adapted to lie against the patient's face; and
   an inflatable member extending substantially completely along said sealing edge and lying between said sealing flap and said sidewall so that inflation of said inflatable member serves to press said sealing flap against the patient's face to effectuate a seal between the face chamber and the patient.

7. The face chamber of claim 5 further including a pressure regulating valve mounted in the upper portion of said sidewall and communicating with said pressure chamber to control the discharge of gases from said pressure chamber to the atmosphere through said pressure regulating valve so as to regulate the pressure maintained in said pressure chamber.

8. The face chamber of claim 1
   wherein said lower portion of said sidewall defines an access opening therethrough sized to permit manual access to the patient's mouth and nose when said face chamber is installed on the patient's face; and,
   closure means for selectively closing said access opening to permit the continuous positive airways pressure source to pressurize the pressure chamber.

9. A face chamber for connection to the pressurized gas outlet of a continuous positive airways pressure source to treat a patient with the gas mixture output therefrom comprising:
   a generally cylindrical, substantially rigid and substantially transparent annular sidewall having a central axis, said sidewall having opposed ends, an upper portion and a lower portion; one of said ends being open and defining a sealing edge thereon contoured to generally conform to the patient's face; said sidewall having a diameter such that the sidewall extends around the patient's face from the chin to the forehead;
   an end wall joined to and closing that end of said sidewall opposite said sealing edge; said end wall being substantially transparent; said end wall including an upper portion oriented generally normal to the sidewall central axis so that the patient may see therethrough when said face chamber is in place on the face of the patient; said end wall further including a lower portion oriented at an acute angle with the central axis of said sidewall and defining an access opening therethrough sized to permit manual access to the patient's mouth and nose when said face chamber is installed on the patient's face;
   closure means for selectively closing said access opening to permit the continuous positive airways pressure source to pressurize the pressure chamber;
   a face seal along said sealing edge of said sidewall adapted to seal the sealing edge to the face of the patient;
   means for holding said sidewall on the face of the patient and maintain said seal in sealing contact with the patient's face,
   said sidewall and said end wall defining a closed pressure chamber about the patient's face while said face chamber is seated against the patient's face so that the patient's face contacts said face chamber only along said seal to free the patient's face and permit the patient to talk and chew without having to remove said face chamber; and
   inlet connection means mounted on the upper portion of said face chamber for connecting the output of the continuous positive airways pressure source to said pressure chamber, said inlet connection means including:
      an L-shaped inlet tube including an inlet leg and a discharge leg joined to one end of and perpendicular to said inlet leg, said inlet and said discharge legs each having a projecting end thereon, said inlet and discharge legs defining a common passage therethrough; and,
      a sealing bushing mounted in the upper portion of said sidewall and defining an opening therethrough slidably receiving said inlet leg of said inlet tube therethrough so that said discharge leg is located in said pressure chamber and so that the projecting end on said inlet leg is located exteriorly of said pressure chamber for connection to the continuous positive airways pressure source, said sealing bushing locating said inlet leg generally radially with respect to said sidewall so that said inlet tube can be moved radially with respect to the sidewall and rotated in said sealing bushing to so that the position at which the gas mixture from the continuous positive airways pressure source is directed onto the patient's face can be moved.

* * * * *